(12) United States Patent
Gupta (10) Patent No.: US 11,684,500 B2
(45) Date of Patent: *Jun. 27, 2023

(54) SYSTEM AND METHOD FOR CONTROLLED DELIVERY OF MEDICAL DEVICES INTO PATIENT BODIES

(71) Applicant: ANCHOR BALLOON, LLC, Portage, MI (US)

(72) Inventor: Vishal Gupta, Portage, MI (US)

(73) Assignee: Anchor Balloon, Inc., Portage, MI (US)

( * ) Notice: Subject to any disclaimer, the term of this patent is extended or adjusted under 35 U.S.C. 154(b) by 331 days.

This patent is subject to a terminal disclaimer.

(21) Appl. No.: 17/249,712

(22) Filed: Mar. 10, 2021

(65) Prior Publication Data
US 2021/0186726 A1 Jun. 24, 2021

Related U.S. Application Data

(62) Division of application No. 16/176,481, filed on Oct. 31, 2018, now Pat. No. 10,980,653.

(51) Int. Cl.
*A61F 2/958* (2013.01)
*A61M 25/10* (2013.01)
(Continued)

(52) U.S. Cl.
CPC .......... *A61F 2/958* (2013.01); *A61M 25/005* (2013.01); *A61M 25/0045* (2013.01);
(Continued)

(58) Field of Classification Search
CPC .... A61M 2025/1079; A61M 2025/105; A61M 2025/09125; A61M 2025/0183;
(Continued)

(56) References Cited

U.S. PATENT DOCUMENTS 5,135,536 A 8/1992 Hillstead
5,141,494 A 8/1992 Danforth et al.
(Continued)

FOREIGN PATENT DOCUMENTS

JP 2015528352 A 9/2015
JP WO2016194550 A1 6/2017
(Continued)

OTHER PUBLICATIONS

Aeby, et al. "A modified technique of balloon anchoring for tricky stent delivery." EuroIntervention, vol. 8, No. 9 (Jan. 2013), pp. 1099-1102. doi: 10.4244/EIJV8I9A168.
(Continued)

*Primary Examiner* — George J Ulsh
(74) *Attorney, Agent, or Firm* — Rosenberg, Klein & Lee (57) ABSTRACT

Intravascular delivery system for deployment of a therapeutic device, such as a stent, in a controlled and robust manner is supported by a lockable balloon catheter equipped with a locking mechanism configured to lock in vivo to a delivery component, such as a guidewire. The lockable balloon catheter can be controllably transitioned between a locked and an unlocked modes of operation by inflation/deflation of the balloon of the lockable balloon catheter. Being in the locked mode of operation, the lockable balloon catheter facilitates delivery of the therapeutic element along the delivery component to a target site while enhancing the stability of the delivery component, especially near the target site.

6 Claims, 8 Drawing Sheets

(51) Int. Cl.
*A61M 25/00* (2006.01)
*A61M 25/09* (2006.01)

(52) U.S. Cl.
CPC .......... *A61M 25/09* (2013.01); *A61M 25/104* (2013.01); *A61M 25/1025* (2013.01); *A61M 2025/09125* (2013.01); *A61M 2025/1079* (2013.01)

(58) Field of Classification Search
CPC .......... A61M 25/0052; A61M 25/1025; A61M 25/104; A61M 25/09; A61M 25/005; A61M 25/0045; A61M 25/10; A61F 2/958
See application file for complete search history.

(56) References Cited

U.S. PATENT DOCUMENTS

| | | | |
|---|---|---|---|
| 5,314,444 | A | 5/1994 | Gianturco |
| 6,685,721 | B1 | 2/2004 | Kramer |
| 10,314,663 | B2 | 6/2019 | Takemoto |
| 10,390,983 | B2 | 8/2019 | Nakaya |
| 2003/0028234 | A1 | 2/2003 | Miller et al. |
| 2004/0133158 | A1 | 7/2004 | Keith et al. |
| 2008/0082050 | A1 | 4/2008 | Solar et al. |
| 2010/0125244 | A1 | 5/2010 | McAndrew |
| 2018/0036158 | A1 | 2/2018 | Nakaya |

FOREIGN PATENT DOCUMENTS

| | | |
|---|---|---|
| JP | 2018019836 A | 2/2018 |
| JP | 2018161415 A | 10/2018 |
| WO | 2014036439 A2 | 3/2014 |

OTHER PUBLICATIONS

Chen, et al. "A simple practical balloon anchoring technique within the guide catheter for chronic total occlusion (CTO) of the coronary artery." J Biomedical Research, vol. 29, No. 5 (Jul. 2015), pp. 423-425. doi: 10.7555/JBR.29.20150068.

Hirokami, et al. "Anchoring technique to improve guiding catheter support in coronary angioplasty of chronic total occlusions." Catheterization and Cardiovascular Interventions, vol. 67, No. 3 (Mar. 2006), pp. 366-371. doi: 10.1002/ccd.20624.

International Search Report and Written Opinion for corresponding PCT Application No. PCT/US2019/052955, dated Dec. 13, 2019.

International Search Report Issued by Foreign Patent Office in Application No. 2021548507.

SYSTEM AND METHOD FOR CONTROLLED DELIVERY OF MEDICAL DEVICES INTO PATIENT BODIES

CROSS-REFERENCE TO RELATED APPLICATION

This application is a division of U.S. patent application Ser. No. 16/176,481, filed Oct. 31, 2018.

FIELD OF THE INVENTION

The present invention is directed to medical devices, and, in particular, to minimally invasive devices which are used for treatment within the human (or animal) body internal passages, such as, for example, vasculature (such as blood vessels), or bile duct, as well as renal ureteric duct, etc.

The subject invention further addresses a delivery system for percutaneous coronary intervention adapted, for example, for intravascular balloon angioplasty.

The present invention is also directed to medical devices designed for intravascular deployment of therapeutic elements, such as, for example, stents, using a balloon catheter that is lockable in vivo to a delivery component, such as a guidewire.

In overall concept, the present invention is directed to a system and method for deployment of a therapeutic element, such as a stent, in a patient's body internal passages (for example, intravascular, or other internal tube-like structures in a patient's body) in a controlled robust manner which permits a reduction of a number of equipment exchanges needed to deploy the therapeutic element at a lesion site within an internal tube-like structure (for example, a blood vessel, in a patient's body) while securing a delivery component, such as a guidewire, within the blood vessel during advancement of the therapeutic element to the lesion site.

Further, the present system is directed to a balloon catheter which is provided with a locking mechanism to lock in vivo to a delivery component, e.g., a guide wire, inserted into the blood vessel under treatment, where the locked balloon catheter facilitates delivery of additional components (such as a therapeutic delivery catheter) along the delivery component (the guidewire) to a target site for treatment while enhancing the stability of the delivery component, when in proximity to the target site.

The present invention is also directed to an intravascular delivery system supported by a balloon catheter equipped with a mechanism to anchor and stabilize a guidewire near the target site for superior delivery of additional intravascular components along the guidewire by minimizing movement of the distal end of the guidewire within the blood vessel, thereby enhancing guidewire stability in vivo.

The present invention is also directed to an intravascular kink resistant delivery system which is reinforced by an external rail (or a buddy system) to help advancement of the additional intravascular device (such as a stent) to the lesion.

In addition, the present invention is directed to a method of using the delivery system where a balloon catheter is delivered to a lesion in a blood vessel over a guidewire and the balloon of the balloon catheter is inflated with a conventional balloon inflation mechanism to dilate the blood vessel and disrupt the lesion. The balloon then is deflated, and moved adjacent to the lesion, and the balloon catheter is locked to the guidewire by inflating the balloon. Subsequently, one or more additional intravascular components may be delivered to the lesion, while the balloon catheter remains locked to the guidewire to anchor and stabilize the guidewire within the blood vessel.

BACKGROUND OF THE INVENTION

Ischemic cardiovascular syndromes affect blood flow by narrowing, weakening, or blocking a blood vessel, often resulting from the buildup of material (referred to herein as a lesion) within the blood vessel. Ischemic cardiovascular syndromes may include the coronary vascular syndrome, sometimes referred to as coronary artery disease (CAD), generally associated with blood vessels leading to/from the heart, as well as the peripheral vascular syndrome, commonly referred to as the peripheral artery disease (PAD), associated with blood vessels which do not lead to/from the heart or the brain.

Endovascular treatment for ischemic cardiovascular syndromes permits access to vascular lesions through percutaneous introduction of catheters through a blood vessel, such as, for example, the femoral artery, and therefore involves less patient trauma than an open surgical approach.

Percutaneous transluminal angioplasty of coronary and peripheral arteries (PTCA and PTA, respectively) are widely accepted as the revascularization procedures of choice in patients with ischemic cardiovascular syndromes (e.g., chronic and acute coronary ischemic syndromes) and peripheral ischemic syndromes (such as the chronic limb ischemia, including claudication and critical limb ischemia).

However, the use of the conventional percutaneous treatments may be limited due to re-occlusion or restenosis. This could be due to the exuberant proliferation of smooth muscle cells that grow to occlude the treated vessel segment, progression of atherosclerotic plaque or negative remodeling of the treated segment causing reoccurrence of symptoms. Re-occlusion, or restenosis, may necessitate potential re-intervention for additional treatment.

Various adjuncts to angioplasty seek to reduce restenosis through numerous techniques. These techniques may include extractional, rotational, orbital, or laser atherectomy, as well as the use of bare metal and bare nitinol stents. More recently, drug eluting stents (DES) started to be used to treat/prevent restenosis. The latter technology has been demonstrated to significantly reduce coronary artery restenosis when compared to angioplasty or bare metal stents.

In peripheral arteries, the use of bare nitinol stents has been shown to be superior to balloon angioplasty alone and has emerged as the "default" percutaneous strategy for the treatment of chronic limb ischemic syndromes, particularly in complex disease patterns involving the femoropopliteal artery.

Stents have been customarily used for treating occlusive vascular disease. For example, U.S. Pat. No. 5,135,536 to Hillstead and U.S. Pat. No. 5,314,444 to Gianturco describe a stent which comprises an expandable wire tube having a reduced diameter for transluminal placement. Once the stent is positioned within a vessel, a balloon catheter is used to expand the stent to support and reinforce the full circumference of the vessel. Such prior art stents typically have high radial strength to resist collapse due to vessel disease.

In the conventional procedure for a stent delivery following percutaneous transluminal angioplasty, initially a guidewire is percutaneously advanced to the lesion within a blood vessel. Subsequently, an angioplasty balloon catheter is advanced over the guidewire to the lesion. The angioplasty balloon catheter may be advanced in an over-the-wire ("OTW") manner or in a rapid exchange ("RX") manner.

When in place, the balloon is inflated to expand the blood flow channel within the blood vessel at the lesion site.

In a subsequent step, the angioplasty balloon catheter is removed from the blood vessel while the guidewire remains in place, and a stent delivery balloon catheter is advanced over the guidewire to the lesion for stent delivery.

A drawback of the conventionally performed procedure is the limited safety and the difficulty of advancing the stent delivery balloon catheter across the lesion, even subsequent to the angioplasty due to the fact that the guidewire does not always constitute a sufficiently stable structure for the catheter advancement in the blood vessel. For example, the free distal tip of the guidewire can uncontrollably move around within the blood vessel. The uncontrollable motion of the distal end of the guidewire may cause its retraction into the guidewire lumen in the stent delivery balloon catheter during advancement within the vessel. This may happen when the blood vessel is tortuous, diffusely diseased, severely calcified, or when there is reduced support from the guiding catheter. If a clinician attempts to advance the stent delivery balloon catheter along an unstable distal free tip of the guidewire, there is a risk of vessel damage, including vessel dissection. Accordingly, a clinician often needs to remove the stent delivery balloon catheter and reintroduce an angioplasty balloon catheter over the guidewire to perform additional angioplasty procedures. This exposes an additional risk for the patient health, reduces efficiency of the procedure, abandonment without placement of the therapeutic device and is extremely expensive.

Given a growing patient population with conditions associated with a substantial vessel wall calcification, especially in patients suffering diabetes and/or chronic kidney disease, need for intravascular therapies increases dramatically. There is a patient population in which current therapies may be inefficient and/or ineffective. Thus, there is a need for an improved intravascular technology that permits intravascular deployment of a therapeutic element, such as a stent, in a controlled and robust manner.

SUMMARY OF THE INVENTION

It is therefore an object of the present invention to provide a system and a method for deployment of a therapeutic element (such as a stent) in a tube-like internal structure in a patient's body, for example intravascular, or other passages, such as the bile duct or ureteric duct, in a controlled and robust manner that would support a reduced number of equipment exchanges needed to deploy the therapeutic device in proximity to a lesion site within a blood vessel, while efficiently securing (anchoring) a delivery component, such as a guidewire, within the blood vessel during advancement of the therapeutic element to the lesion site.

It is another object of the present invention to provide a locking mechanism for releasably securing the balloon catheter in vivo to a delivery component, e.g., a guidewire, so that the balloon catheter, being secured to the guidewire, facilitates the delivery of additional components, e.g., a therapeutic delivery catheter, along the guidewire to a target site while enhancing the stability of the guidewire in the blood vessel, especially near the target site.

It is an additional object of the present invention to provide an intravascular delivery system which prevents the guidewire's distal end from uncontrollable motion throughout the vessel lumen, providing a sufficient rigidity and stability of the guidewire in proximity to the target (lesion) site within a blood vessel, which is beneficial for delivery of a therapeutic element, e.g., a stent to the target site.

It is a further object of the present invention to provide an intravascular delivery system using a lockable balloon catheter equipped with a locking mechanism operating to anchor and stabilize the guidewire near the target site within the blood vessel for superior delivery of additional intravascular components along the guidewire, resulting in a reduced displacement of the distal end of the guidewire within the blood vessel, thus attaining enhanced guidewire stability in vivo.

It is also an object of the present invention to provide a method of using the subject balloon catheter controllably lockable to a guidewire within the blood vessel of interest for delivering the balloon catheter to a lesion in the blood vessel over a guidewire, inflating the balloon with a conventional balloon inflation system to pre-dilate the vessel and disrupt the lesion (such as, for example, calcified plaque, disposed on the luminal lining), subsequently deflating the balloon for displacement adjacent to the lesion, and locking the balloon to the guidewire by re-inflating the balloon. One or more additional intravascular components may be subsequently delivered to the lesion site while the subject balloon catheter remains locked to the guidewire which, in its turn, is anchored and stabilized within the vessel during the procedure.

In addition, it is an object of the present invention to provide a kink resistant intravascular delivery system where the shaft of the catheter is enhanced with an additional support and/or a rail mechanism for advancement of intravascular components along the guidewire while the balloon is in the locked or unlocked configuration.

In accordance with one aspect of the subject system, an intravascular system is provided for securely advancing a stent over a guidewire to a lesion within a blood vessel (or the bile duct or the ureteric duct) of a patient. The subject system may include an elongated catheter shaft having a proximal region, a distal region, an inflation lumen extending internal of the elongated catheter shaft between the proximal region and the distal region, and a guidewire lumen which extends between a rapid-exchange (RX) port formed within the elongated catheter shaft and a distal tip of the balloon catheter.

A balloon is affixed at the distal region of the elongated catheter shaft. A proximal end of the balloon is positioned a short distance of about 5 mm-30 mm apart from the rapid-exchange (RX) port. This arrangement attains stability in advancement of the stent along the guidewire to the lesion site within the blood vessel proximal to the rapid-exchange port while the balloon remains inflated within the blood vessel.

A locking portion of the elongated catheter shaft is disposed inside the balloon and extends between the proximal and distal ends of the balloon. The locking portion of the elongated catheter shaft may be configured to transition within the balloon from an unlocked mode of operation (when a diameter of the guidewire lumen is sized to permit its slidable displacement relative to the guidewire disposed within the guidewire lumen) to a locked mode of operation. In the locked mode of operation, the locking portion of the elongated catheter shaft is compressed within the balloon to reduce the diameter of the guidewire lumen, so that the walls of the guidewire lumen come into contiguous contact with the guidewire and become circumferentially coupled to and compress the guidewire to "anchor" the guidewire within the guidewire lumen.

The locking portion of the elongated catheter shaft may include a flexible material to facilitate the compression of the guidewire with the walls of the guidewire walls. The flexible material may include a braided material. The braided material may be a metal composition and the braided material may be coated with a polymer such that the locking portion of the elongated catheter shaft within the balloon is fluid impermeable.

The balloon catheter may have a plurality of radiopaque markers disposed along the elongated catheter shaft. The radiopaque markers may be positioned adjacent to the rapid-exchange port.

In accordance with another aspect of the subject system, a method is provided for safe advancement of an intravascular delivery system over a guidewire along the balloon shaft to a lesion within a blood vessel of a patient. The method may include the steps of:

fabricating a balloon catheter lockable to a guidewire within the blood vessel. The lockable balloon catheter includes an elongated catheter shaft having a proximal region, a distal region, a first lumen extending between the proximal region to the distal region, and a second lumen extending distally from a rapid-exchange (RX) port within the elongated catheter shaft.

A balloon is affixed to the elongated catheter shaft at the distal region such that a proximal end of the balloon is displaced from the rapid-exchange port a short distance of about 5 mm-30 mm to attain a stable advancement of the therapeutic element (stent) over the delivery component (guidewire) to the target site within the body lumen proximal to the rapid-exchange port while the balloon remains inflated within the body lumen.

The elongated catheter shaft may be configured to transition within the balloon from an unlocked mode of operation (when a diameter of the second lumen is sized to permit the slidable movement of the delivery component (guidewire) therein), to a locked state (when the elongated catheter shaft is compressed within the balloon to reduce the diameter of the second lumen to circumferentially contact the delivery component (guidewire) to lock the delivery component (guidewire) within the second lumen, responsive to pressurization within the balloon).

The subject method further includes the steps of:
delivering the lockable balloon catheter to the lesion in the blood vessel over the guidewire;
inflating a balloon of the lockable balloon catheter to dilate the blood vessel and disrupt the lesion;
deflating the balloon;
displacing the deflated balloon on the balloon catheter past the lesion within the blood vessel; and
locking the balloon catheter to the guidewire by re-inflating the balloon.

Inflating the balloon compresses the walls of the second lumen within the balloon around the guidewire to lock the guidewire in place, and thus locks the balloon catheter to the guidewire.

The subject method continues by delivering another catheter (for example, a stent catheter) over the guidewire to the lesion site while the lockable balloon catheter remains locked to the guidewire to anchor and stabilize the guidewire within the blood vessel.

The subject system and method reduces the number of equipment exchanges needed to deploy the therapeutic devices at a lesion site within the blood vessel, while securing the delivery component within the blood vessel during advancement of the therapeutic catheter to the lesion site.

These and other objects and advantages of the subject system and method will become more apparent to a person of ordinary skill in the art upon reading the Detailed Description of the Subject Invention in conjunction with the Patent Drawings.

BRIEF DESCRIPTION OF THE DRAWINGS

FIGS. 3A, 3B and 3C are schematic representations of the distal region of the subject lockable balloon catheter shown in FIG. 1 depicted, respectively, in the unlocked state (FIG. 3A) and the locked state (FIG. 3B), while FIG. 3C depicts a longitudinal cross-section of the subject lockable balloon catheter in the locked mode of operation;

DETAILED DESCRIPTION OF THE PREFERRED EMBODIMENT

FIGS. 1-4D and 5A-5L depict a system for deployment of a therapeutic device within a tube-like internal structure of a patient's body (such as a blood vessel (body lumen), or the bile duct, as well as ureteric duct, etc.). Although the principles of the subject system and method are applicable for treatment procedures associated with different internal passages (tube-like structures) within a patient's body, the following description of the subject system design and operation will be focused on the intravascular applications.

The subject system includes a balloon catheter which is capable of locking in position in vivo to a delivery component, such as, for example, a guidewire, disposed within a blood vessel. Subsequent to locking the lockable balloon catheter to the guidewire, another catheter for delivery of a therapeutic device, such as a stent, may be advanced over the guidewire to a target site in the blood vessel while the locking balloon catheter stably anchors the guidewire in place adjacent to the target site in the blood vessel.

The subject system is particularly well-suited for treating conditions associated with vessel wall tortuosity, diffuse disease, calcification or poor guiding catheter support during ischemic cardiovascular syndromes including the coronary vascular syndrome, sometimes referred to as coronary artery disease (CAD), as well as the peripheral vascular syndrome, sometimes referred to as the peripheral artery disease (PAD).

Figure 1:
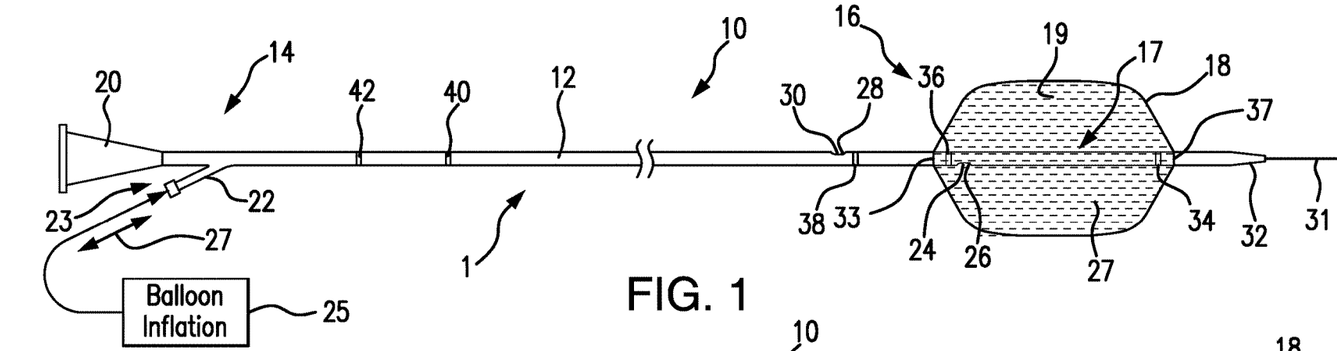
FIG. 1 depicts an exemplary embodiment of the subject lockable balloon catheter.

Referring to FIG. 1, the subject intravascular delivery system 1 includes a balloon catheter 10 which includes an elongated shaft 12 extending between a proximal region 14 and a distal region 16 of the balloon catheter 10. A balloon 18 is mounted to the elongated shaft 12 at the distal region 16. The elongated shaft 12 has a portion 17 extended inside the balloon 18 (further referred to herein as a locking portion 17).

The proximal region 14 of the elongated shaft 12 preferably includes a handle 20 for helping a clinician to manipulate the lockable balloon catheter 10.

Figure 3A:
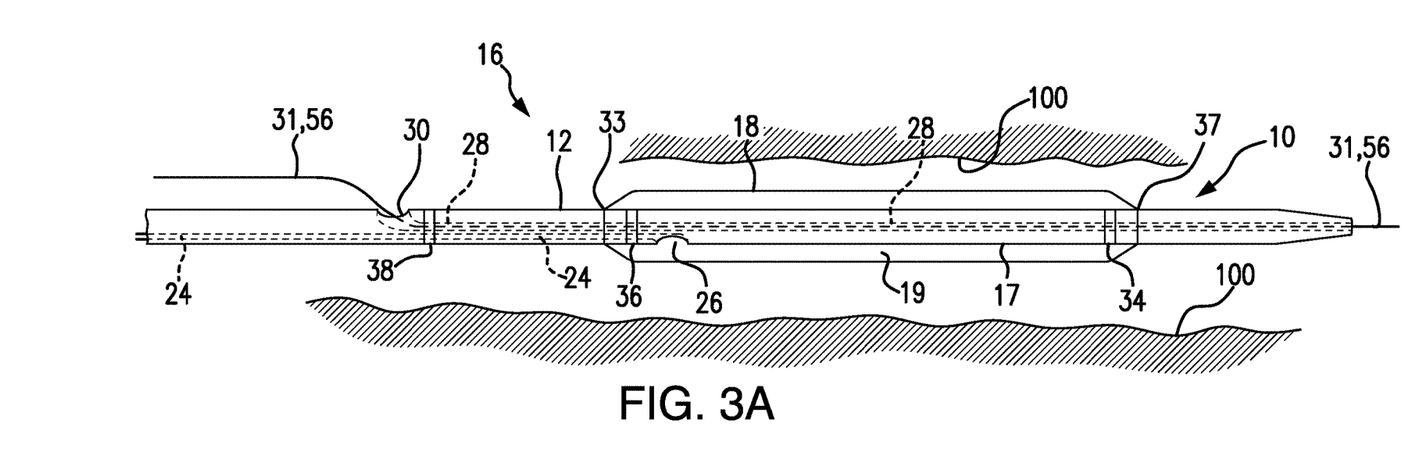
Figure 3B:
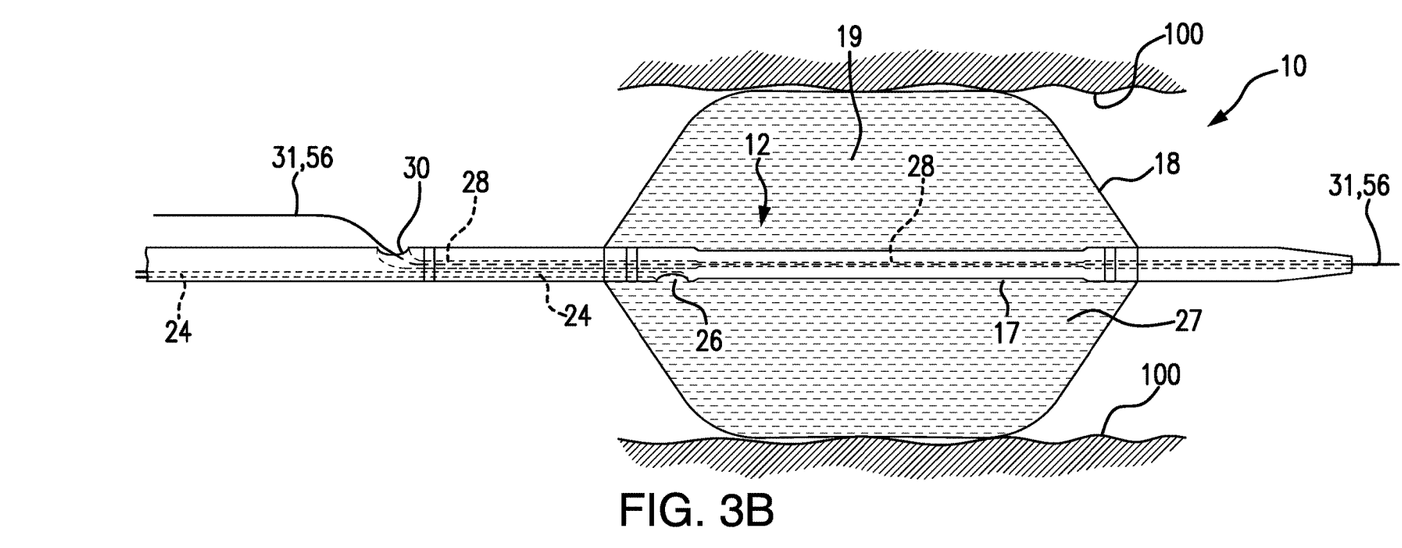
Figure 3C:
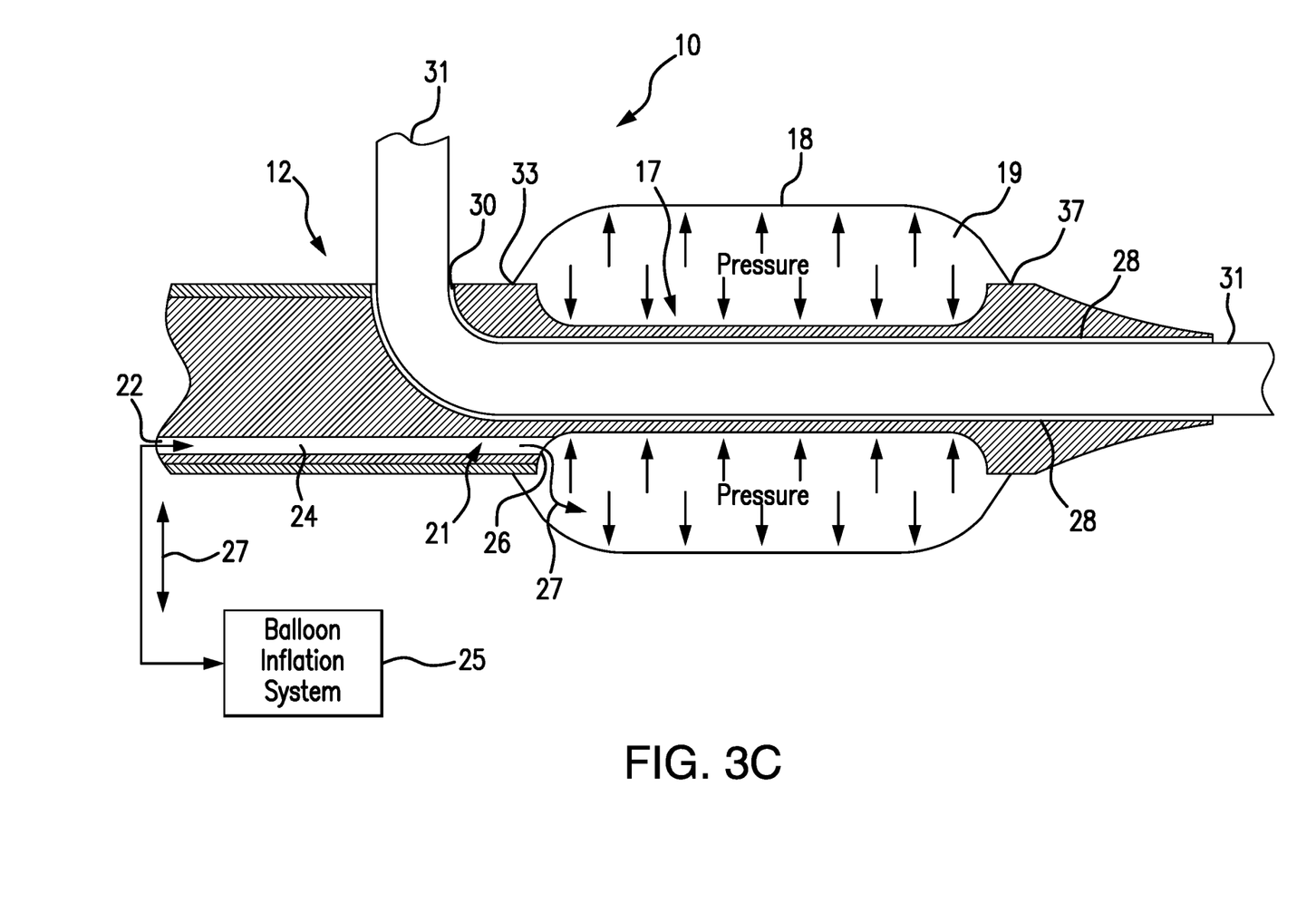

A balloon inflation port 22 at the proximal end 23 of the proximal region 14 is coupled to the interior 19 of the balloon 18 through an inflation lumen 24 extending within the elongated shaft 12, as depicted in FIGS. 3A-3C.

The handle 20 and the balloon inflation port 22 may be elements used in conventional balloon catheters, and are not detailed herein with further specifics. Similar to the proximal region 14 of the subject lockable balloon catheter 10, the handle 20 and the balloon inflation port 22 may be formed from materials conventionally used in the intravascular catheters, e.g., polyethylene and/or polyterephthalate.

The lockable balloon catheter 10 preferably has a length and diameter suitable for use in a cardiac or peripheral vessel under treatment. The balloon catheter 10 may have the length ranging from 60 cm to 180 cm and a diameter ranging from 1.0 mm to 60 mm.

The balloon 18 may assume a closed (deflated) configuration (shown in FIGS. 3A and 4A, 4C, 5B, 5D-5E, and 5H-5I), or an inflated (expanded) configuration (shown in FIGS. 1-2, 3B-3C, 4B, 4D, 5C, and 5F-5G). Shown in FIG. 1, the balloon 18 is depicted in an expanded configuration suitable for dilating the blood vessel. The balloon 18 may be formed of a noncompliant material (such as polyethylene), a semi-compliant material (such as polyterephthalate), or a compliant material (such as nylon).

The balloon 18 may be sized and shaped for insertion in the blood vessel as appropriate for an intended therapy and a bodily lumen (blood vessel) under treatment. For example, the length of the balloon 18 may range from 1 cm to 20 cm. The balloon 18 may have a diameter, in the expanded configuration, of about 1.0 mm-6.0 mm for insertion in smaller lumens (such as coronary vessels). Alternatively, the balloon 18 may have a diameter of about 4 mm-10 mm for insertion in larger lumens (such as peripheral vessels). The balloon 18 may also have a diameter of about 1 cm-6 cm if the catheter 10 is used for the therapy associated with the thoracic or abdominal aorta.

The balloon 18 is preferably affixed to the locking portion 17 of the elongated shaft 12 via thermal bonds, glue welds, or other suitable methods.

The balloon 18 is configured to expand when it is pressurized responsive to the introduction of a fluid (air) through the balloon inflation port 22 under control of a balloon inflation system 25.

The balloon inflation system 25 is operatively coupled to the balloon inflation port 22 in a fluidly sealed fashion to support passage of the inflation fluid 27 (such as, for example, saline, iodinated contrast media, or air) to and from the balloon 18.

The balloon inflation system 25, which is schematically depicted in FIG. 1, may be a manual or an automatic system. In the preferred automatic embodiment, the balloon inflation system 25 may include an electronic sub-system, a pneumatic sub-system, and a control software with a corresponding user interface. The electronic sub-system, under control of the control software, supplies power to solenoid pressure valves (which are fluidly coupled to the balloon inflation port 22) to control the pressurizing/depressurizing cycles of the operation of the subject balloon system with the air flow.

The inflation lumen 24 is configured with and terminates, at its distal end, in a balloon inflation port 26, which is disposed within the interior 19 of the balloon 18, preferably, in proximity to the balloon's proximal end 33. The inflation lumen 24 extends internally of the elongated shaft 12 between the balloon inflation port 22 and the balloon 18 to provide bi-directional passage of the fluid (air) therealong for pressurizing/de-pressurizing of the balloon 18.

In the pressurized state, the balloon 18 assumes the expanded (inflated) configuration (shown in FIGS. 1, 2, 3B-3C, 4B, 4D, 5C, and 5F-5G). While in the depressurized state, the balloon 18 assumes a deflated (closed) configuration (shown in FIGS. 3A, 4A, 4C, 5B, 5D, 5E, 5H, 5I, and 5J).

The subject intravascular delivery system 1 operates in conjunction with a delivery component 31, such as, for example, a guidewire. The guidewire 31 is advanced inside the blood vessel towards (and preferably beyond) the lesion site prior to the cardiac (or other intravascular) procedure. The intravascular delivery system 1 is subsequently displaced along the guidewire 31 internally of the blood vessel to a position corresponding to a lesion site for pre-dilatation, or other treatment.

The lockable balloon catheter 10 is configured with a guidewire lumen 28 extending internally the elongated shaft 12 between the rapid-exchange (RX) port 30 and the tapered tip 32. The guidewire 31 extends inside the guidewire lumen 28 and extends distally beyond the tapered tip 32.

The guidewire lumen 28 is sized to permit the passage of the guidewire 31 therethrough. For example, the guidewire lumen 28 may be sized to permit the guidewire to be inserted therethrough to facilitate displacement of the distal region 16 to a desired location along the guidewire 31 in a patient's vasculature or an organ.

As shown in FIG. 3C, the guidewire lumen 28 may be located centrally in the elongated shaft 12, or alternatively, may be off-center. Preferably, the guidewire lumen 28 is compressible responsive to actuation of the balloon inflation system 25 by a clinician, e.g., inflation of balloon 18, to lock the guidewire 31 therein, as will be detailed in further paragraphs.

The elongated shaft 12 may preferably be formed of a flexible material to facilitate compression of the guidewire lumen 28. The elongated shaft 12 may be formed of a flexible material along its entire length, or along a select portion(s) of its length, such as the locking portion 17 within the balloon 18.

In the subject system 1, the lockable balloon catheter 10 is equipped with a locking mechanism which includes and is supported by cooperation of the balloon inflation system 25, inflation lumen 24, balloon 18, and locking portion 17 of the elongated shaft 12 to transform the subject system between the locked mode of operation and the unlocked mode of operation.

In the locked mode of operation, the inflation of the balloon 18 is used to lock the balloon catheter 10 to the guidewire 31. As an example, the inflation of the balloon 18 at a predetermined pressure (e.g., a high pressure), causes the locking portion 17 of the elongated shaft 12 to press against the guidewire 31 (as depicted in FIGS. 3B-3C, 4B, and 4D), thereby causing the walls of the guidewire lumen 28 (extending from the RX port 30 into the balloon 18) to compress around the delivery guidewire 31, thus locking the guidewire 31 within the elongated shaft 12. In the compressed configuration, the contiguous coupling between the walls of the guidewire lumen 28 and the guidewire 31 prevents relative displacement between the guidewire 31 and the elongated shaft 12. Thus, the contiguous coupling between the walls of the guidewire lumen 28 and the guidewire 31 resulted from the controlled pressurizing of the balloon 18, as needed by the therapeutic procedure, locks the guidewire 31 to the elongated shaft 12 of the balloon catheter 10.

When the inflation system 25 of the locking mechanism deflates the balloon, the walls of the guidewire lumen 28 return to their original configuration, thus releasing the guidewire from the coupling with the elongated shaft 12, thereby transitioning into the unlocked mode of operation. In the unlocked mode of operation, the guidewire and the elongated shaft 12 are free to be displaced one relative to the other.

The RX (Rapid Exchange) port 30 is formed at the elongated shaft 12 a short distance from the proximal end 33 of the balloon 18. This arrangement permits the delivery of a therapeutic delivery catheter along the guidewire 31 to a target site in a blood vessel while the balloon catheter 10 remains locked to the body lumen, as shown in FIGS. 5G-5J, and as will be detailed in further paragraphs.

For example, while a typical rapid-exchange port is conventionally displaced at least 15 cm from a balloon, the RX port 30 in the subject system 1 may be disposed much closer, e.g., about 1-5 mm to 30 mm from the subject balloon's proximal end 33.

The compactness of the subject structure has a beneficial result, since the guidewire 31 exits from the elongated shaft 12 via the RX port 30 within the blood vessel, and the therapeutic delivery catheter can be positioned in proximity to the RX port 30 and the balloon 18 while the balloon 10 remains securely locked to the guidewire 31 in the body lumen, thus providing favorable stable conditions for stent delivery. The therapeutic delivery catheter is thus anchored and stabilized within the body lumen.

The subject balloon catheter 10 may include one or more radiopaque markers to facilitate positioning of the balloon catheter 10 under fluoroscopic imaging. As shown in FIG. 1, the balloon catheter 10 includes radiopaque markers 34, 36, 38, 40, and 42 positioned along the elongated shaft 12. The radiopaque markers may be fabricated from conventional materials, such as platinum or iridium. The radiopaque markers 34 and 36 are positioned adjacent to the distal end 37 and the proximal end 33 of the balloon 18, respectively, for visualizing the location of the balloon 18 in the blood vessel. The radiopaque marker 38 is positioned adjacent to the RX port 30 to permit visualization of the location of the RX port 30. The radiopaque markers 40 and 42 are shaft markers and may be displaced about 90 and 100 cm, respectively, from the distal end (tip) 32 of the elongated shaft 12.

Figure 2:
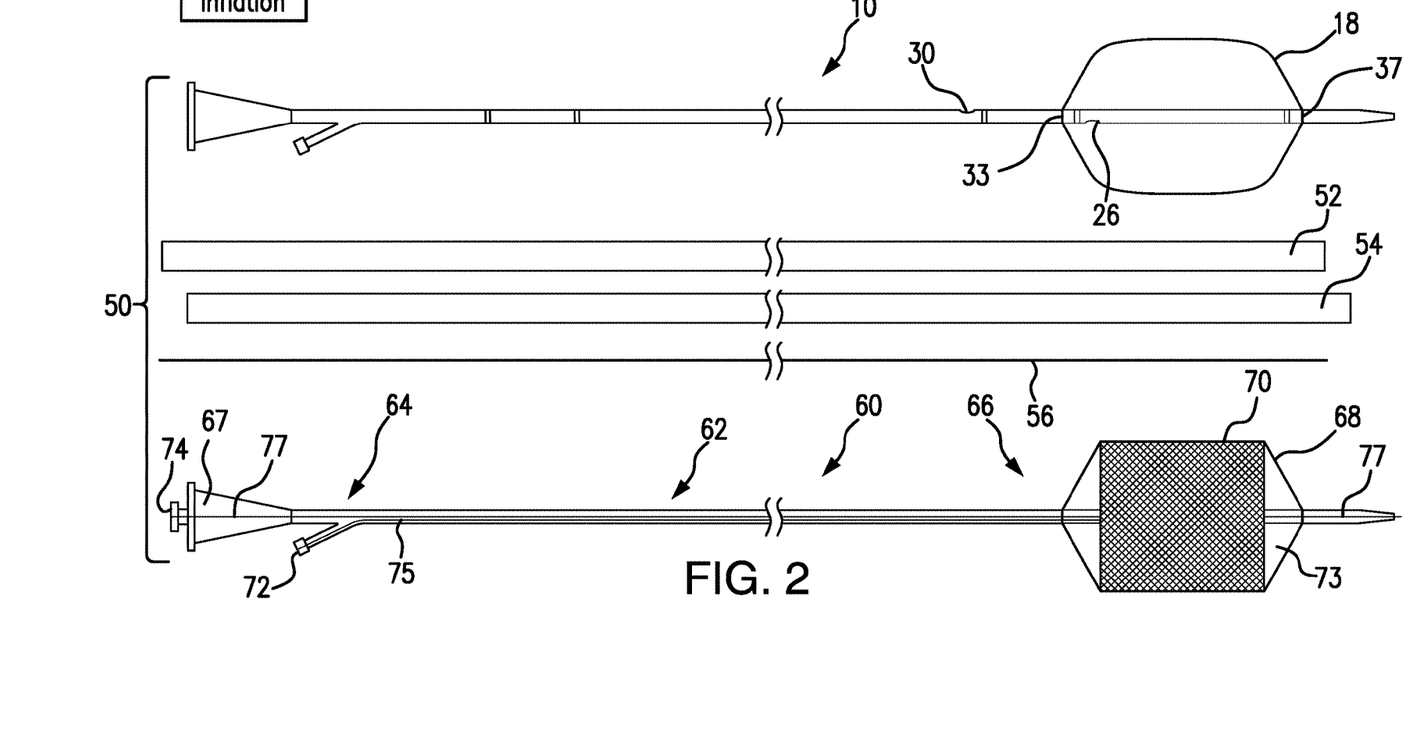
FIG. 2 depicts an exemplary embodiment of the subject system intravascular delivery which includes a therapeutic delivery catheter, sheaths, and a guidewire, for use with the balloon catheter shown in FIG. 1.

FIG. 2 shows an alternative configuration of the subject intravascular delivery system which uses the lockable balloon catheter 10 shown in FIG. 1. The system includes a therapeutic delivery catheter, one or more sheaths, and the delivery component. In the illustrated example, shown in FIG. 2, the system 50 includes the lockable balloon catheter 10, a sheath 52, a sheath 54, a delivery component (guidewire) 56, and a therapeutic delivery catheter 60.

The sheath 52 is sized and shaped for intravascular delivery procedure. The sheath 52 constitutes a lumen to permit the lockable balloon catheter 10 to be disposed therein for a delivery procedure.

The sheath 54 is sized and shaped for intravascular delivery and constitutes a lumen to permit the therapeutic delivery catheter 60 to be disposed therein for the intravascular delivery. The sheaths 52 and 54 may be conventional sheaths used in intravascular procedures.

The delivery component 56 is sized and shaped for the intravascular delivery procedure, and may be a guidewire, as illustrated. In one example, the delivery component 56 is a conventional guidewire used in intravascular procedures.

The therapeutic delivery catheter 60 is designed to intravascularly deliver a therapeutic device (such as a stent) to a target site in a body lumen. The therapeutic delivery catheter 60 includes an elongated shaft 62 having a proximal region 64 and a distal region 66. A balloon 68 is mounted at the distal region 66 of the elongated shaft 62.

The proximal region 64 of the elongated shaft 62 is manipulated by a clinician. For this purpose, the proximal region 64 is equipped with a handle 67. A balloon inflation port 72 is coupled to the interior 73 of the balloon 68 through an inflation lumen 75 extending internally along the elongated shaft 62.

A guidewire port 74 is coupled to the distal region 66 of the elongated shaft 62 through a guidewire lumen 77. The guidewire lumen 77 is sized to receive the guidewire 56 therein.

The handle 67 and the ports 72 and 74 are conventional elements, and similar to the proximal region 64 of the therapeutic delivery catheter 60, may be formed from materials conventionally used for fabrication of intravascular catheters, e.g., polyethylene or polyterephthalate. The therapeutic delivery catheter 60 preferably has a length and diameter suitable for use in the therapeutic procedures associated with cardiac or peripheral vessels.

The therapeutic delivery catheter 60 is configured to deliver a therapeutic device 70, which may be, for example, a stent. In the example, depicted in FIG. 2, the therapeutic delivery catheter 60 includes the balloon 68 disposed at a predetermined location at the distal region 66 of the elongated shaft 62 within the therapeutic device 70. When the balloon 68 is expanded (as the result of introducing the fluid (or air) into the balloon inflation port 72), it causes the therapeutic device 70 to expand from a delivery (deflated) configuration to a deployed (expanded) configuration.

While the therapeutic delivery catheter 60 is depicted in the exemplary embodiment as a balloon catheter for stent delivery (e.g., bare metal stent or drug-eluting stent), the therapeutic delivery catheter 60 may also deliver other types of therapeutics and may be, for example, a drug-delivery catheter, a balloon catheter, a drug-eluting balloon catheter, or an energy delivery catheter. Examples of drugs that may be delivered include anti-mitotic drugs, regenerative agents, anti-inflammatory agents, anti-allergenic agents, anti-bacterial agents, anti-viral agents, anticholinergic agents, antihistamines, antithrombotic agents, anti-scarring agents, anti-proliferative agents, antihypertensive agents, anti-restenosis agents, healing promoting agents, vitamins, proteins, genes, growth factors, cells, stem cells, vectors, RNA, and/or DNA. The energy delivery catheter may include numerous types of energy, including the ultraviolet light, ultrasound, resistive heat, radio frequency (RF), and cryogenic.

FIGS. 3A, 3B, and 3C depict the distal region 16 of one embodiment of the subject lockable balloon catheter 10. FIGS. 3A and 3B show, respectively, the balloon catheter 10 in the unlocked state (FIG. 3A) and the locked state (FIG. 3B), while FIG. 3C shows the longitudinal cross-section of the subject balloon catheter 10 in its locked state.

In FIG. 3A, the elongated catheter shaft 12 is in the unlocked state (mode of operation). In the unlocked state, the diameter of the guidewire lumen 28 is sized to support the slidable movement (displacement) of guidewire 31 therein.

The elongated shaft 12 is designed to transition to the locked state, shown in FIGS. 3B-3C, by compressing the locking portion 17 of the elongated shaft 12 inside the balloon 18 to reduce the diameter of the guidewire lumen 28 when the balloon 18 is inflated, so that the walls of the elongated shaft 12, at its locking portion 17, circumferentially embrace and press on the guidewire 31 to lock the guidewire 31 within the guidewire lumen 28. For example, introduction of the fluid (air) into the balloon 18 via the inflation lumen 24 and the balloon inflation port 26 inflates the balloon 18 and pressurizes the internal space 19 of balloon 18 to a level that compresses the walls of the locking portion 17 of the elongated catheter shaft 12, as shown in FIGS. 3B and 3C.

Advantageously, the inflation of the balloon 18, in addition to coupling the guidewire lumen 28 to the guidewire 31, may also increase the coupling of the walls of the balloon 18 with the inner lining of the body lumen 100, thereby anchoring the balloon 18 within the body lumen to stabilize the locked guidewire 31 within the body lumen 100, as shown in FIGS. 3A-3B.

Figure 4A:
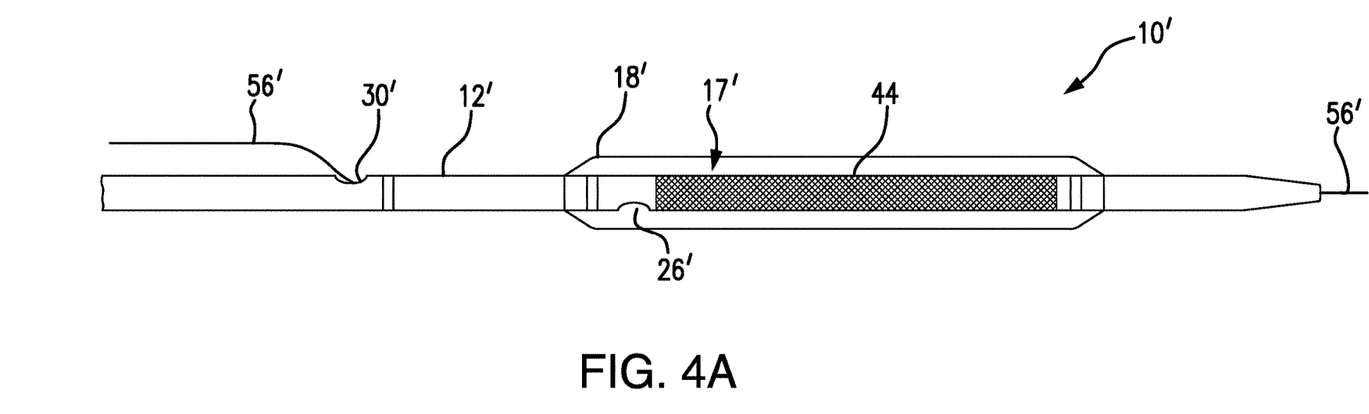
FIGS. 4A and 4B are schematic representations of the distal region of an alternative embodiment of the subject balloon catheter formed with a flexible material at the locking portion of the subject catheter within the balloon to facilitate the operation of the subject lockable balloon catheter in the unlocked mode of operation (FIG. 4A) and the locked mode of operation (FIG. 4B), respectively.
Figure 4B:
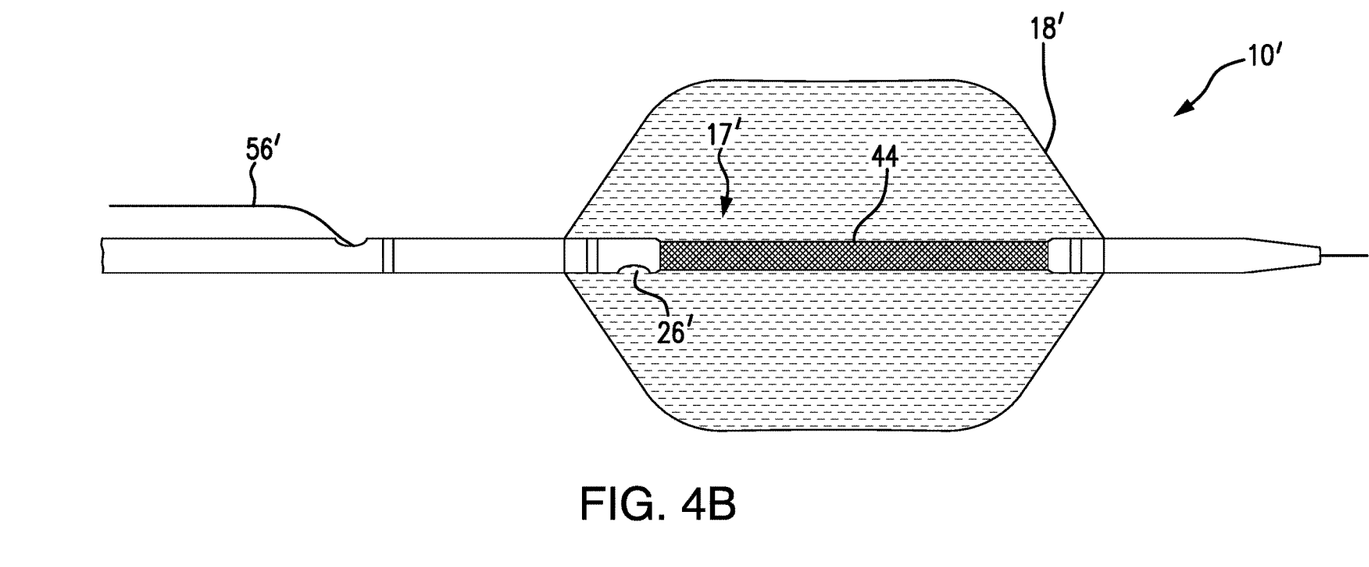

FIGS. 4A and 4B depict the distal region of a catheter 10' similar to that shown in FIGS. 3A, 3B, and 3C. The catheter 10' includes a flexible material 44 at the locking portion 17' of the elongated shaft 12' within the balloon 18' to facilitate the locking mechanism. The lockable balloon catheter 10' is fabricated in the configuration similar to the lockable balloon catheter 10 shown in FIGS. 1-2 and 3A-3C, so that similar components are indicated with similar number with prime. The flexible material 44 may extend along the elongated shaft 12' only within balloon 18' (only at the locking portion 17') or may extend further along the entire length of the elongated shaft 12'. The flexible material 44 may be formed from a braided material, e.g., braided metal, such as stainless steel. The braided material may be coated with another fluid impermeable material, such as a polymer. As is shown, the flexible material 44 at the locking portion 17' is configured to compress upon actuation, e.g., inflating and pressurizing of the balloon 18, thereby locking the guidewire lumen to the delivery component 56'.

Figure 4C:
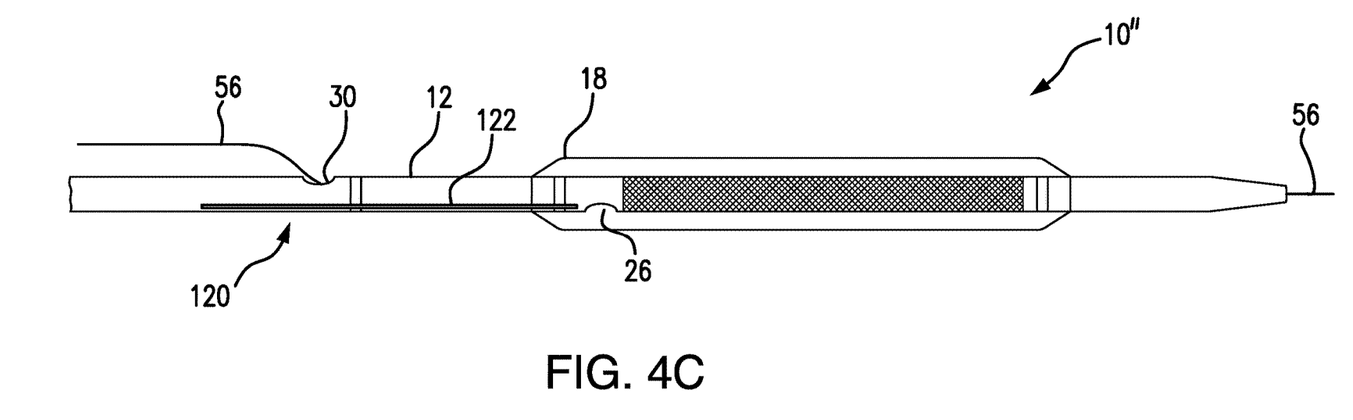
FIGS. 4C-4D show schematically a wire-like kink resistant mechanism (FIG. 4C) or an alternative kink resistant mechanism attached at the RX port (FIG. 4D) embedded at the distal region of the elongated shaft between the RX port and the balloon.
Figure 4D:
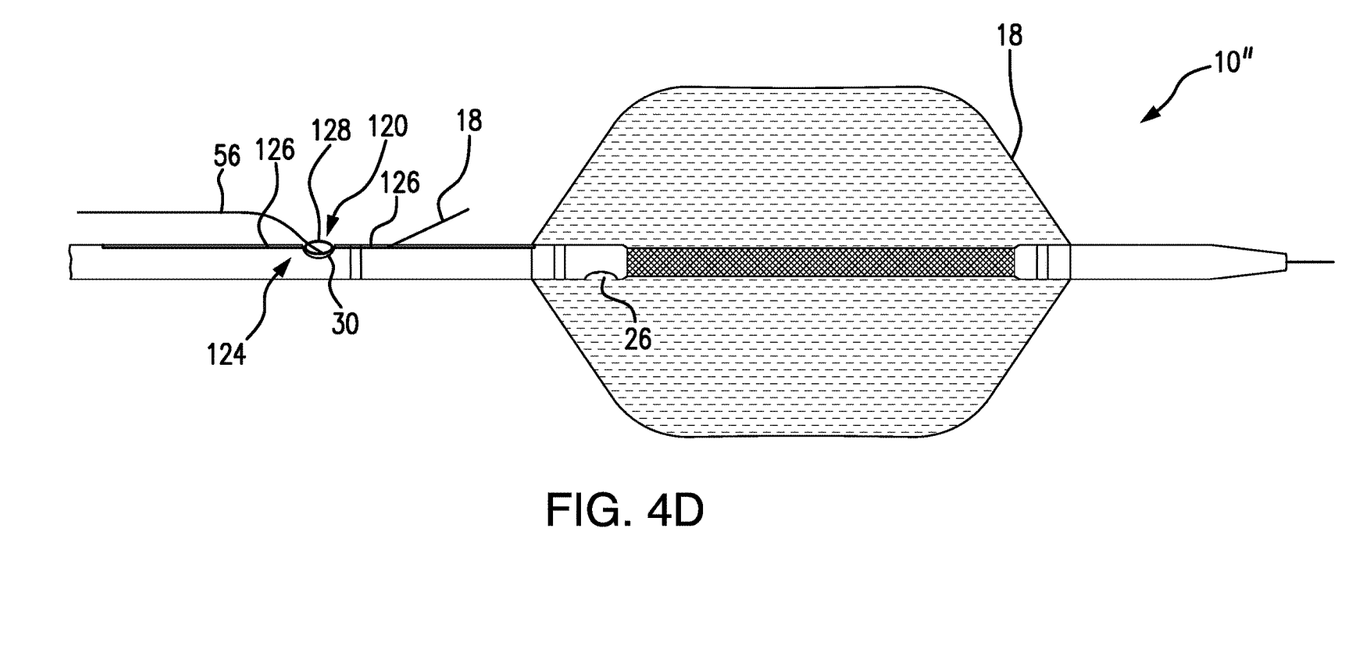

Referring to FIGS. 4C-4D, in an alternative implementation, the subject balloon catheter 10" may be enhanced by a kink resistant mechanism 120. A portion of the subject system between the RX port 30 and the balloon 18, is vulnerable to possible sharp twists, buckling, and/or curving of the elongated catheter shaft 12 when the inflated balloon 18 is pulled along the guidewire as another delivery device (stent) is advanced over the guidewire.

In order to prevent the unwanted deviation of the elongated catheter shaft 12 from the straight configuration during the cardiac procedure, the subject system 10", in its alternative implementation, is configured with the kink resistant mechanism 120. The kink resistant mechanism 120 may be formed with a Nitinol/Steel wire-like member (or stamped elongated member) 122 affixed internally along the elongated catheter shaft 12 between the RX port 30 and the balloon 18 (as shown in FIG. 4C). Alternatively, the kink resistant mechanism 120 may be formed from Nitinol/Steel as an elongated member 124 configured with elongated parts 126 connected (preferably integrally therewith) through a central circular (or oval) shaped part 128. The elongated member 124 may be embedded in the wall of the elongated catheter shaft 12, as well as may be attached internally or externally along the elongated catheter shaft 12 (as shown in FIG. 4D) with the central part 128 secured to the RX port 30 in alignment with the periphery of the RX port 30.

Alternatively, the kink resistant mechanism 120 may be represented by both members 122 and 124 (combined embodiment) embedded in the wall of the elongated catheter shaft 12 or secured (internally or externally) to the wall of the elongated catheter shaft 12 between the RX port 30 and the balloon 18.

In either configurations, either embedded, or secured internally or externally, or in the combined embodiment, the kink resistant mechanism 120 prevents sharp twisting, buckling, and curling of the elongated catheter shaft 12, and thus provided a robust system capable of withstanding various scenarios of cardiac procedures.

Although shown in FIGS. 4C-4D in application to the embodiment depicted in FIGS. 4A-4B, the kink resistant mechanism 120 is applicable to all alternative embodiments of the subject system shown in FIGS. 1-5I.

The subject method may use the lockable balloon catheter 10 and 10' to perform an interventional procedure. However, only as an example, the subject method is described infra for use with the lockable balloon catheter 10 depicted in FIGS. 1, 2, and 3A-3C. The alternative catheters 10' shown in FIGS. 4A-4B may also be used in a manner similar to that described below.

Figure 5A:
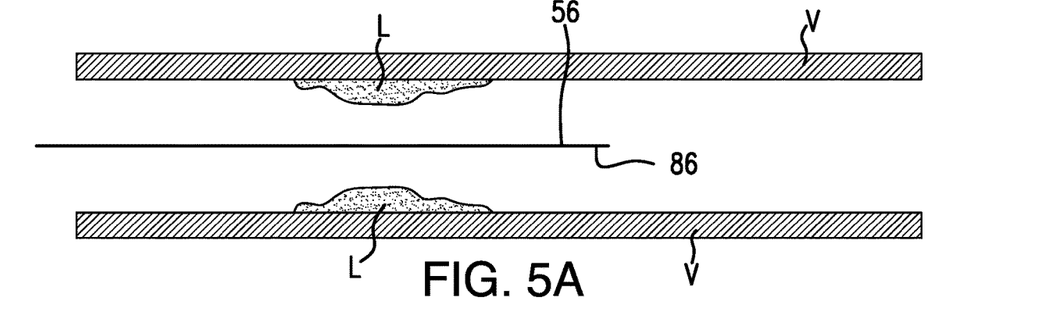
FIGS. 5A-5L illustrate the exemplary steps of the intravascular delivery procedure using the subject lockable balloon catheter to deliver a therapeutic device to a target site within a blood vessel.

In FIG. 5A, delivery component (guidewire) is advanced inside the blood vessel and is delivered to a target location. In this example, the delivery component 56 (illustratively, a guidewire) is placed in the vessel V at the location of a lesion L as determined by the fluoroscopic imaging technique, contrast agents and/or conventional interventional techniques.

Figure 5B:
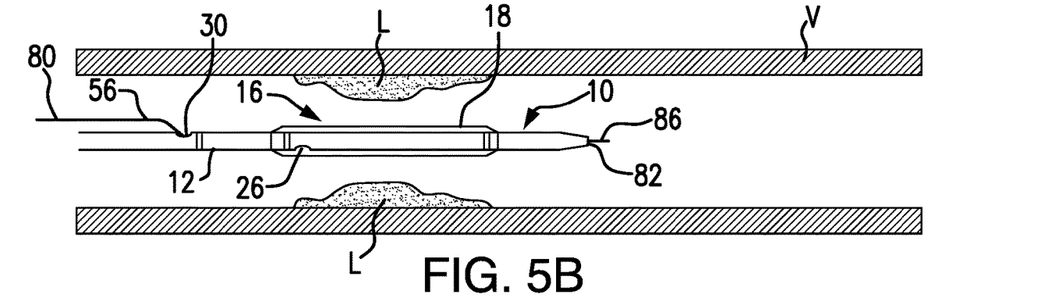

As shown in FIG. 5B, the balloon catheter 10 is back-loaded onto the delivery component 56 by inserting the proximal end 80 of the guidewire 56 into the distal opening 82 of the guidewire lumen 28 located in the distal tip 32 of the balloon catheter 10. The catheter 10 is advanced through the patient's vasculature V until the distal region 16 is disposed at the target location (e.g., the lesion L), as determined using the radiopaque markers on the catheter shaft 12 and the fluoroscopic imaging. When so disposed in a patient's vessel V, the distal region 16 of the balloon catheter 10 will appear as depicted in FIG. 5B. During the delivery procedure, the balloon 18 of the catheter 10 may be wrapped or folded in the closed configuration.

Alternatively, a delivery sheath (such as sheath 52 shown in FIG. 2) may be disposed over the distal region 16 of the balloon catheter 10 to attain a smooth outer surface for the lockable balloon catheter 10. The sheath 52 then may be retracted proximally to expose the distal region 16 once it has reached the desired location L in vessel V. As shown, the guidewire 56 is disposed in the guidewire lumen 28 within the balloon 18 and exits the catheter 10 at the guidewire RX port 30.

Figure 5C:
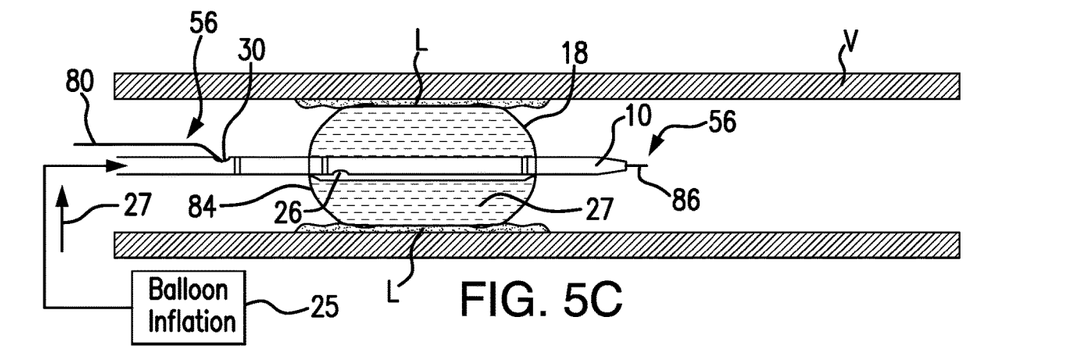
Figure 5D:
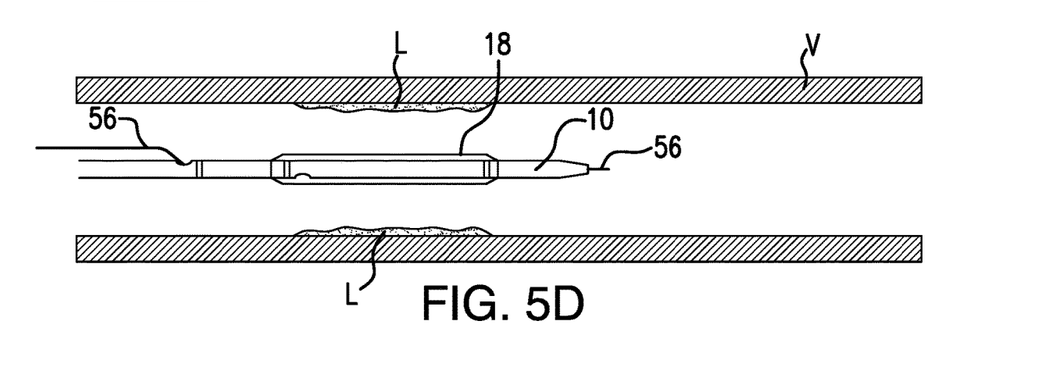

Referring now to FIGS. 5C and 1, a conventional inflator system 25 is coupled to the inflation port 22, and the inflation medium 27, such as, for example, saline or a saline diluted iodinated contrast agent, is delivered via the inflation lumen 24 to the balloon 18 to cause the balloon's expansion. In the inflated configuration, the walls 84 of the balloon 18 contact the lesion L and the intima of the vessel V to dilate the vessel V and disrupt the lesion L. Subsequently, as shown in FIG. 5D, the balloon 18 is deflated.

Figure 5E:
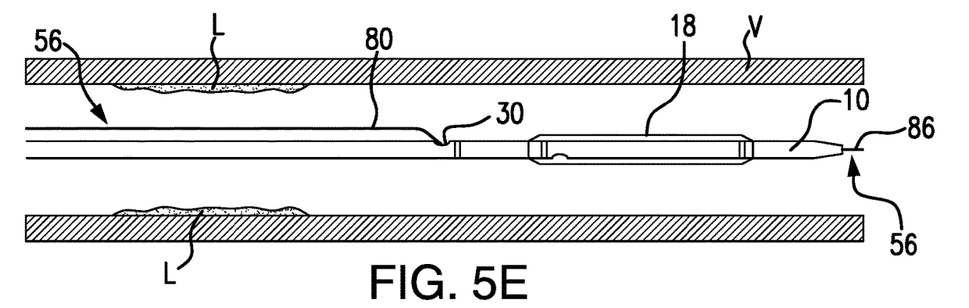

Referring now to FIG. 5E, the balloon 18, in its deflated configuration, is advanced along the distal end 86 of the guidewire 56 to a location adjacent to, but beyond, the target site L within the body lumen V. For example, the lockable balloon catheter 10 and the delivery component 56 may be moved distally within the vessel V such that the RX port 30 is disposed distal to the target site L, and the proximal end 80 of the delivery component (guidewire) 56 is located outside of the catheter 10 and extends through the target site within the body lumen V.

Figure 5F:
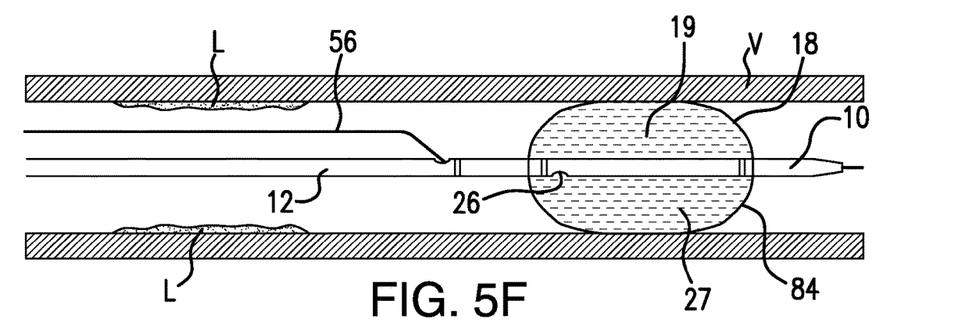

Subsequently, as shown in FIG. 5F, the balloon catheter 10 is locked to the delivery component 56 by introduction of the fluid 27 into the balloon 18 via the inflation lumen 24 and the balloon inflation port 26. Introduction of the fluid 27 under high pressure inflates the balloon 18 and pressurizes the internal space 19 of the balloon 18 to a level that compresses the elongated catheter shaft 12 and forces the guide lumen 28 into tight contact with the delivery component 56 contained therein, thus compressing around the delivery component 56 and locking the delivery component 56 to the elongated shaft 12. In addition, the inflation of the balloon 18 causes the walls 84 of the balloon 18 with or without a contiguous contact with the internal lining of the vessel V, thereby anchoring the balloon 18 within the vessel V to stabilize the locked delivery component 56 within the vessel V.

Figure 5G:
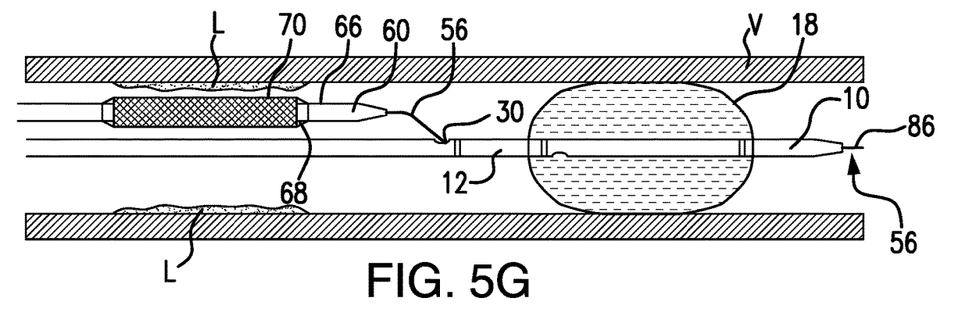

As presented in FIG. 5G, when the balloon catheter 10 is locked to the delivery component 56, and the balloon catheter 10 and the delivery component 56 are anchored in place within the body lumen (with or without contact of the walls 84 of the balloon 18 with the internal lining of the blood vessel V), the therapeutic delivery catheter 60 may be delivered along the delivery component 56 to align the therapeutic device 70 with the target site L. During delivery, the balloon 68 of therapeutic delivery catheter 60 may be folded. Alternatively, a delivery sheath (such as the sheath 54 shown in FIG. 2) may be disposed over the distal region 66 of the catheter 60 to form a smooth outer surface for the therapeutic delivery catheter 60. The sheath 54 subsequently may be retracted proximally to expose the distal region 66 once it reaches the desired location in the vessel V. In the body lumen, the lockable balloon catheter 10 remains separate from the therapeutic delivery catheter 60, although both use the same delivery component 56 in the lumen V.

Figure 5H:
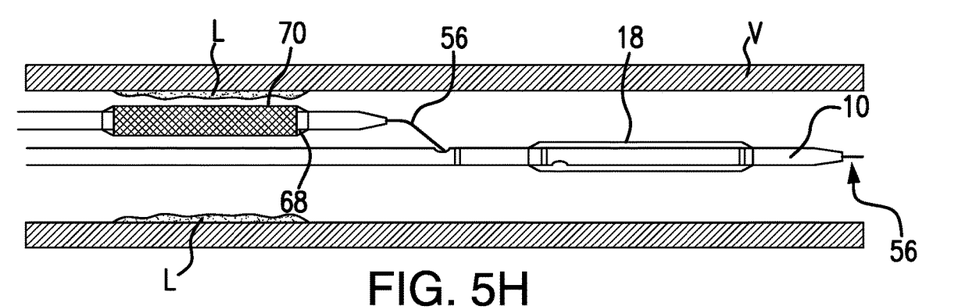

Subsequently, as shown in FIG. 5H, the lockable balloon catheter 10 is unlocked from the delivery component 56. For example, deflation of the balloon 18 may result in decompression of the elongated shaft 12 so that the diameter of the guidewire lumen 28, at its locking part 17, expands to permit slidable displacement of the guidewire 56 therewithin.

Figure 5I:
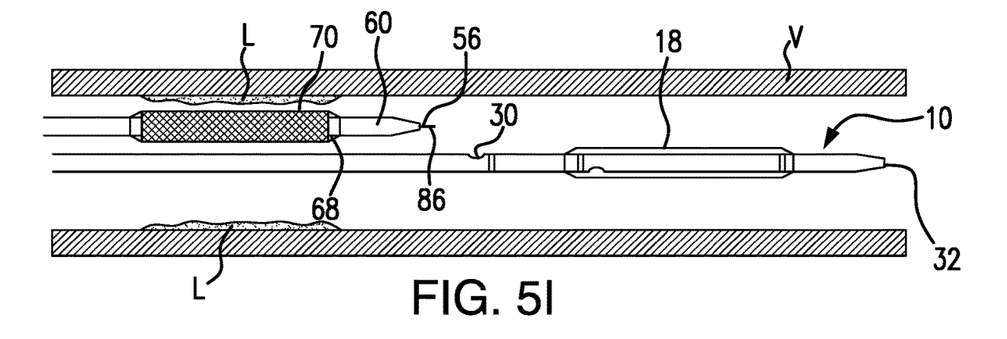

As shown in FIG. 5I, the delivery component (guidewire) 56 is then removed from the lockable balloon catheter 10. For example, the delivery component 56 may be pulled proximally while the lockable balloon catheter 10 is held in place until the distal end 86 of the delivery component 56 exits the RX port 30. Alternatively, the lockable balloon catheter 10 can be moved distally while the delivery component 56 is held in place until the distal end 86 of the delivery component 56 exits the RX port 30.

Figure 5J:
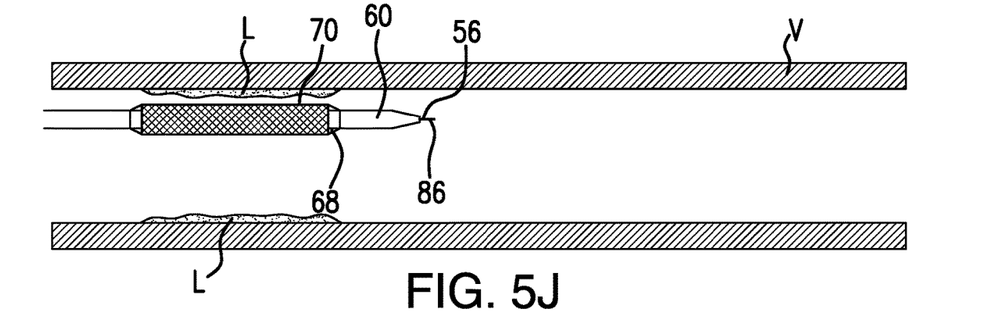

As shown in FIG. 5J, the lockable balloon catheter 10 is then displaced proximally past the target site L while the therapeutic delivery catheter 60 remains positioned at the target site L within the blood vessel V. The lockable balloon catheter 10 may be removed entirely from the patient's blood vessel V, or may be displaced a suitable proximal distance to permit the therapeutic deployment. Alternatively, the balloon catheter may be moved to a different vessel or a branch of the vessel V.

Figure 5K:
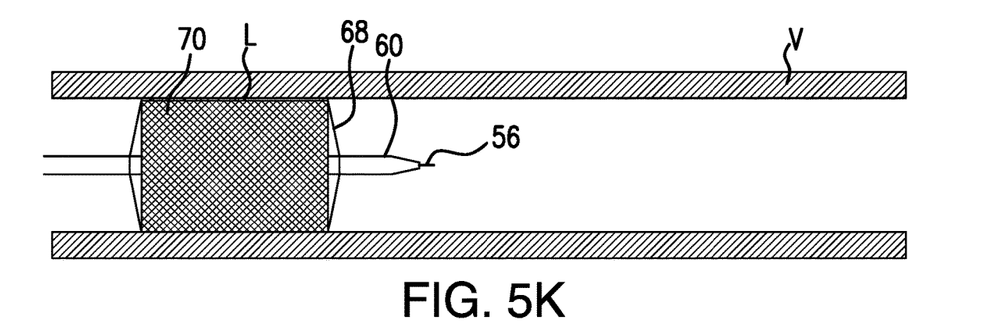

As shown in FIG. 5K, the therapeutic device (stent) 70 is then deployed at the target site L. For example, the balloon 68 may be inflated to expand, thereby causing the therapeutic device 70 to expand and contact the inner wall of the vessel V.

Figure 5L:
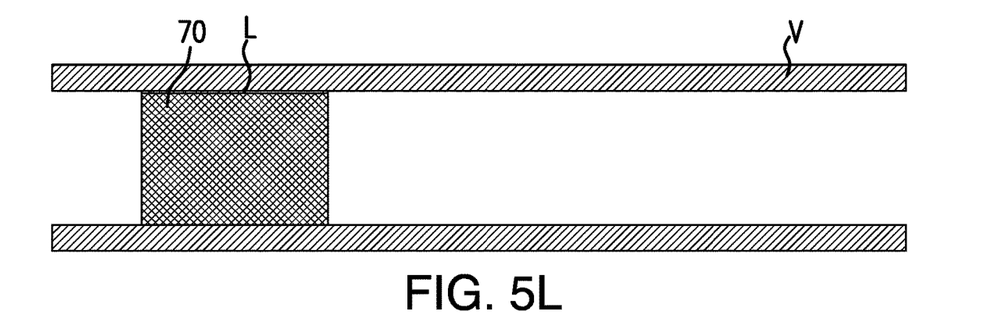

Subsequently, as shown in FIG. 5L, in the case when the therapeutic device (stent) 70 is designed for implantation, the therapeutic delivery catheter 60 is removed, leaving the therapeutic device 70 implanted at the target location L.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method for intravascular delivery of a therapeutic device by secure advancement along a guidewire to a lesion site within a blood vessel of a patient, the method comprising:
   configuring at least a lockable balloon catheter including:
   an elongated catheter shaft having a proximal region, a distal region, and a rapid-exchange (RX) port formed in walls of said elongated catheter shaft between said proximal and distal regions thereof,
   an inflation lumen extending within said elongated catheter shaft from said proximal region to said distal region,
   a guidewire lumen extending distally from said RX port within the elongated catheter shaft to and along said distal region;
   a balloon having a proximal and a distal end and secured to said elongated catheter shaft at the distal region, said proximal end of said balloon being displaced from said RX port a predetermined distance; and
   a locking mechanism operatively coupled between said balloon and said elongated catheter shaft, said locking mechanism being configured to transition said elongated catheter shaft between an unlocked configuration, when a diameter of the guidewire lumen permits slidable movement of the guidewire therein, and a locked configuration, when, responsive to inflation of said balloon, walls of said elongated catheter shaft are compressed to reduce the diameter of the guidewire lumen to circumferentially contact the guidewire to prevent displacement of said guidewire within the guidewire lumen;
   delivering said lockable balloon catheter to the lesion site in the blood vessel over a guidewire;
   inflating said balloon of said lockable balloon catheter to dilate the blood vessel and disrupt the lesion;
   deflating said balloon, and moving said balloon adjacent to the lesion site within the blood vessel;
   re-inflating said balloon, thus locking said balloon catheter to the guidewire; and
   delivering a second catheter over said guidewire to the lesion site.

2. The method of claim 1, wherein the second catheter comprises a stent, the method further comprising the step of:
   delivering the stent at the lesion site within the blood vessel.

3. The method of claim 2, further comprising the step of:
prior to delivering the stent, removing said lockable balloon catheter from the blood vessel.

4. The method of claim 1, wherein the second catheter is delivered while the balloon catheter remains locked to the guidewire to anchor and stabilize the guidewire within the blood vessel within said lockable balloon catheter.

5. The method of claim 1, wherein locking of said lockable balloon catheter to said guidewire comprises the step of inflating said balloon.

6. The method of claim 5, wherein inflation of said balloon causes compression of said walls of said guidewire lumen within said balloon around the guidewire.

* * * * *